(12) United States Patent
Huang

(10) Patent No.: US 10,458,889 B2
(45) Date of Patent: Oct. 29, 2019

(54) DETECTING MACHINE FOR A YIELD RATE OF BRISTLES OF A TOOTHBRUSH AND DETECTING METHOD FOR BRISTLES OF A TOOTHBRUSH

(71) Applicant: ACUMEN CO., LTD., New Taipei (TW)

(72) Inventor: Shou Jen Huang, New Taipei (TW)

(73) Assignee: ACUMEN CO., LTD., New Taipei (TW)

( * ) Notice: Subject to any disclaimer, the term of this patent is extended or adjusted under 35 U.S.C. 154(b) by 0 days.

(21) Appl. No.: 15/902,571

(22) Filed: Feb. 22, 2018

(65) Prior Publication Data

US 2019/0195761 A1    Jun. 27, 2019

(30) Foreign Application Priority Data

Dec. 25, 2017    (TW) .............................. 106145458 A

(51) Int. Cl.
| | | |
|---|---|---|
| *G01N 3/16* | (2006.01) | |
| *A46D 1/04* | (2006.01) | |
| *A46D 99/00* | (2006.01) | |
| *A46D 3/04* | (2006.01) | |

(52) U.S. Cl.
CPC .............. *G01N 3/165* (2013.01); *A46D 1/04* (2013.01); *A46D 99/00* (2013.01); *A46D 3/042* (2013.01); *G01N 2203/0019* (2013.01); *G01N 2203/0037* (2013.01)

(58) Field of Classification Search
CPC ........... G01N 2203/0087; G01N 3/165; G01N 2203/0019; G01N 2203/0037; A46D 1/04; A46D 99/00; A46D 3/042; A46B 17/00; A46B 9/04

USPC .......................................................... 73/821
See application file for complete search history.

(56) References Cited

U.S. PATENT DOCUMENTS

| | | | | |
|---|---|---|---|---|
| 4,320,774 A | * | 3/1982 | Rogers .................... | A46B 5/06 15/22.1 |
| 4,884,311 A | * | 12/1989 | Gergory .................. | A46B 9/04 15/167.1 |
| 5,042,107 A | * | 8/1991 | Gregory .................. | A46B 9/04 15/167.1 |
| 6,079,087 A | * | 6/2000 | Cansler .................... | A46D 1/00 28/247 |
| 7,222,382 B2 | * | 5/2007 | Choi ........................ | A46B 9/04 15/23 |
| 9,066,580 B2 | * | 6/2015 | Marichi Rodriguez ..................... A46B 9/045 |

(Continued)

*Primary Examiner* — Octavia Hollington
(74) *Attorney, Agent, or Firm* — R. Lynette Wylie; Apex Juris, Pllc.

(57) ABSTRACT

A detecting machine for a yield rate of bristles of a toothbrush and a detecting method for the bristles are provided. The detecting machine includes a power device and two rotating units, and the two rotating units are rotatably mounted on a side surface of the power unit. The two rotating units are disposed parallel to each other. When in a rotating condition, the two rotating units rotate in opposite rotating directions. When a manufacturer horizontally disposes a toothbrush between the two rotating units, the surfaces of the two rotating units may compress the bristles and pull the bristles toward a direction away from the toothbrush. Therefore the manufacturer can inspect whether the bristles are firmly mounted on the toothbrush.

2 Claims, 4 Drawing Sheets

(56) References Cited

U.S. PATENT DOCUMENTS 9,956,063 B2 * 5/2018 Hauser .................... A46B 9/04

* cited by examiner

DETECTING MACHINE FOR A YIELD RATE OF BRISTLES OF A TOOTHBRUSH AND DETECTING METHOD FOR BRISTLES OF A TOOTHBRUSH

CROSS-REFERENCE TO RELATED APPLICATIONS

This application is based upon and claims priority under 35 U.S.C. 119 from Taiwan Patent Application No. 106145458 filed on Dec. 25, 2017, which is hereby specifically incorporated herein by this reference thereto.

BACKGROUND OF THE INVENTION

1. Field of the Invention

The present invention relates to a detecting machine and a detecting method for a toothbrush, especially to a machine and a method that detects the stability of bristles detached on a head of the toothbrush.

2. Description of the Prior Arts

A common method for attaching bristles onto a head of a toothbrush comprises two steps. First, bend a tuft of bristles into an U-shaped structure by a sheet metal, and press the tuft of bristles by the sheet metal, wherein an opening of the U-shaped bristles faces upwards, so two ends of the U-shaped bristles extend upwardly, meanwhile the metal sheet presses the bristles downwardly between the two ends of the U-shaped bristles. Second, mount the bristles and the sheet metal securely in a head of a toothbrush. Two opposite ends of the sheet metal are then mounted securely in the head of the toothbrush to fix the position of the U-shaped bristles in the toothbrush.

However, during this manufacturing process, the bristles can be easily detached from the head of the toothbrush if the sheet metal is not properly pressing the bristles. This defect may shorten a service life of an end product of the toothbrush However, during the current manufacturing process of the toothbrushes, the finished products are only detected by an X-ray machine. Through the X-ray machine, the manufacturer can only confirm whether the sheet metal is mounted in the toothbrush with the bristles, but cannot distinguish if the metal sheet is properly pressing the bristles.

Therefore, the manufacturer cannot distinguish the properly mounted bristles from the improperly mounted bristles through the seemly identical appearances.

Consequently, when the defective toothbrush is used by consumers, the bristles of the defective toothbrush may be easily detached from the head of the toothbrush under normal usage.

Therefore, the conventional detecting machines for the bristles of the toothbrush and the detecting method for the same are both defective.

To overcome the shortcomings, the present invention provides a detecting machine for a yield rate of bristles of a toothbrush and a detecting method for bristles of the toothbrush to mitigate or obviate the aforementioned problems.

SUMMARY OF THE INVENTION

The main objective of the present invention is to provide a detecting machine for a yield rate of bristles of a toothbrush and a detecting method for the bristles of the toothbrush. The method includes steps of pulling the bristles by two rotating units which are constantly rotating in opposite directions, so the two rotating units generate a force slightly pulling the bristles away from the head of the toothbrush to detect whether the bristles are firmly mounted on the head of the toothbrush.

The detecting machine for a yield rate of bristles of a toothbrush has a power device and two rotating units. The two rotating units are rotatably mounted on a side surface of the power unit, disposed parallel to each other, and capable of being driven by the power device to rotate respectively. In a rotating condition, the two rotating units rotate in opposite rotating directions, a tuft of the bristles of the toothbrush is moved to a position between the two rotating units, and surfaces of the two rotating units jointly compress the tuft of bristles.

The detecting method for bristles of a toothbrush comprises steps as follows. Move a tuft of the bristles of the toothbrush to a position between two rotating units. Rotate the two rotating units in different rotating directions respectively. Compress two opposite sides of the tuft of bristles respectively, so the surfaces of the two rotating units will then pull the bristles toward a direction away from a head of the toothbrush.

Given the foregoing structure of the detecting machine for a yield rate of bristles of a toothbrush and a detecting method for the bristles of the toothbrush, when the bristles of a toothbrush is disposed at a position between the two rotating units, wherein the two rotating units are rotating constantly in opposite directions, the surfaces of the two rotating units may jointly compress the bristles of the toothbrush from two opposite sides of the bristles and pull the two sides away from the head of the toothbrush. By doing so, if the sheet metal is not properly pressing the bristles, the bristles will be pulled out from the head of the toothbrush during the detecting process. In other words, the manufacturer can distinguish the properly produced toothbrush from the improperly produced toothbrush more precisely by inspecting the degree of the bristles remaining on or detached from the head of the toothbrush after completion of the detecting process. Therefore, by the aforementioned detecting machine and detecting method, the manufacturer can raise the accuracy of the detection.

Other objectives, advantages and novel features of the invention will become more apparent from the following detailed description when taken in conjunction with the accompanying drawings.

DETAILED DESCRIPTION OF THE PREFERRED EMBODIMENTS

Figure 1:
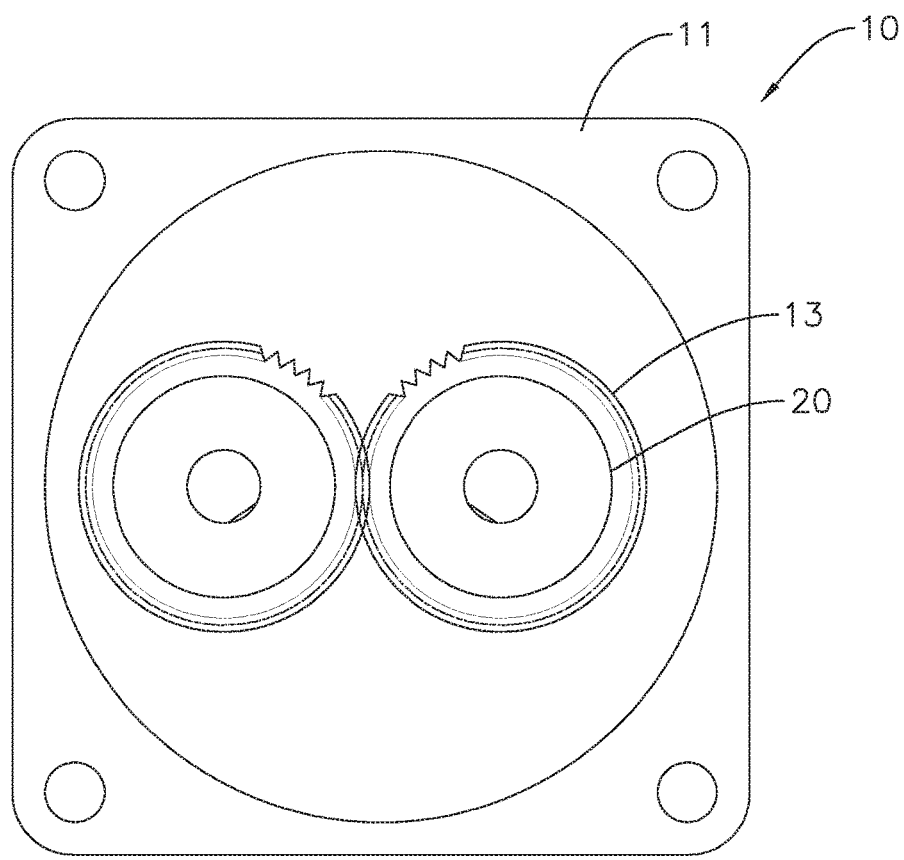
FIG. 1 is a front view of a detecting machine in accordance with the present invention.

With reference to FIG. 1, a detecting machine for a yield rate of bristles of a toothbrush in accordance with the present invention comprises a power device 10 and two rotating units 20. The two rotating units 20 are rotatably mounted on a side surface the power device 10. The two rotating units 20 are disposed parallel to each other. The two rotating units 20 are capable of being driven by the power device 10 to rotate respectively.

Figure 2:
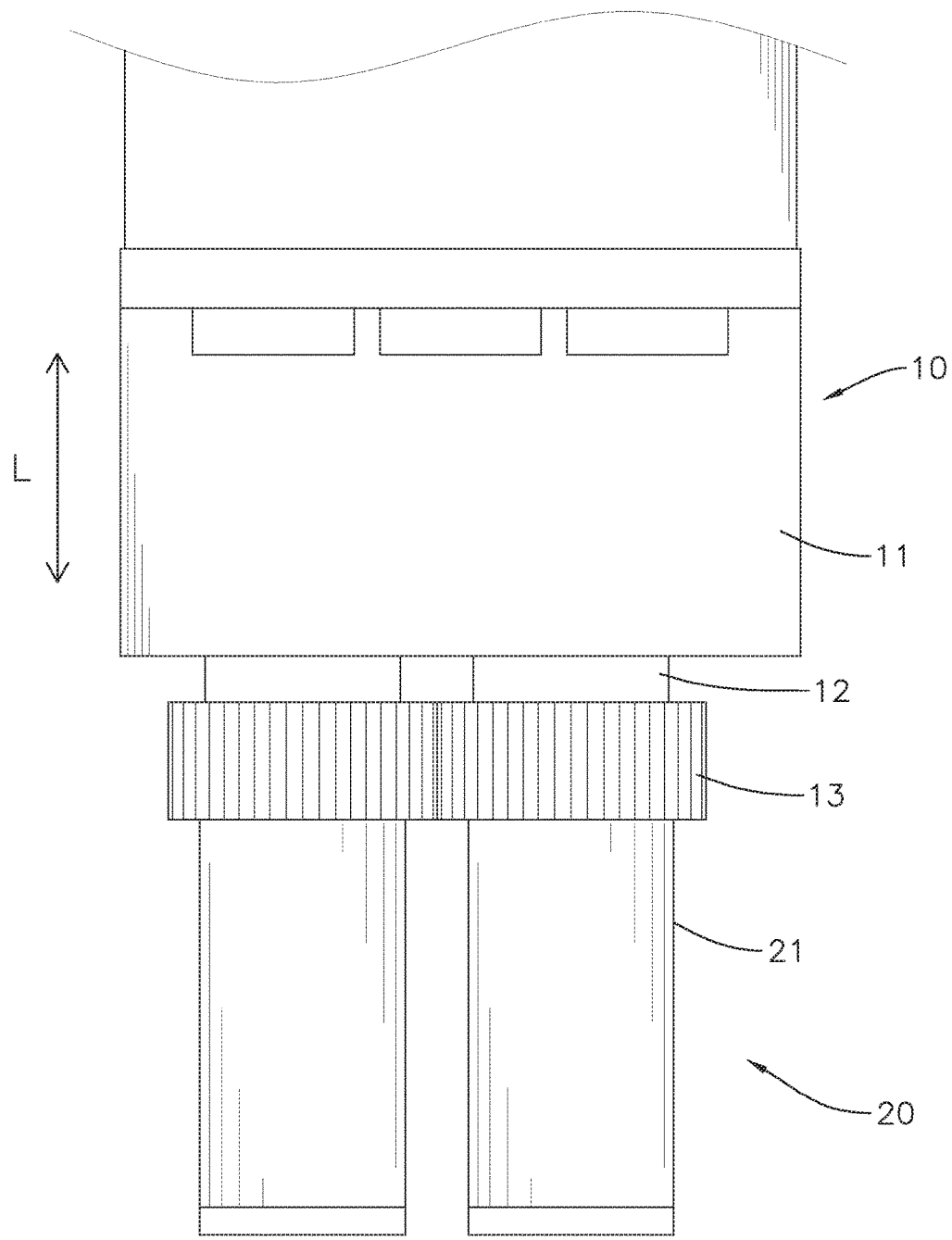
FIG. 2 is a top view of the detecting machine in FIG. 1.

With reference to FIG. 1 and FIG. 2, the power device 10 comprises a motor 11, two transmitting rods 12 and two transmitting gears 13.

The two transmitting rods 12 are rotatably mounted on the motor 11 respectively. One of the two transmitting rods 12 is capable of being driven by the motor 11 to rotate. The two transmitting gears 13 are mounted on the two transmitting rods 12 respectively. The two transmitting gears 13 engage with each other. Therefore, when the transmitting rod 12 that is capable of being driven by the motor 11 starts rotating, the transmitting gear 13 mounted on said transmitting rod 12 rotates in the same direction with said transmitting rod 12. Consequently, the other transmitting gear 13, which is engaging with the aforementioned transmitting gear 13, will then rotate in an opposite direction and drives the transmitting rod 12 that is mounted with said transmitting gear 13 to rotate in the same direction. In other words, the two transmitting rods 12 are capable of being driven to rotate in opposite directions through the structure that one of the two transmitting rods 12 is driven by the motor 11 and through the engagement of the two transmitting gears 13, but it is not limited thereto. The two transmitting rods can be driven to rotate in opposite directions by other means.

Moreover, the power device in the present invention may also be a non-automatic power device. For example, the two transmitting rods can be driven by a rotating shaft and a handle which may be rotated manually.

With reference to FIG. 1 and FIG. 2, the two rotating units 20 are connected to the power device 10 respectively. The two rotating units 20 are arranged apart from each other. Specifically, the two rotating units 20 are connected to the two transmitting rods 12 respectively and may be driven by the transmitting rods 12 to rotate. In the present embodiment, each one of the two rotating units 20 is, but not limited to, a cylinder, as the rotating units 20 may also be in other shapes. The two rotating units 20 are disposed parallel to each other when being connected to the two transmitting rods 12 respectively.

Furthermore, in the present invention, the two rotating units 20 are disposed parallel to each other, but it is not limited thereto, as the two rotating units 20 may also be disposed obliquely. The disposition of the two rotating units 20 may be designed according to the shape of the bristles of the toothbrush.

Figure 3:
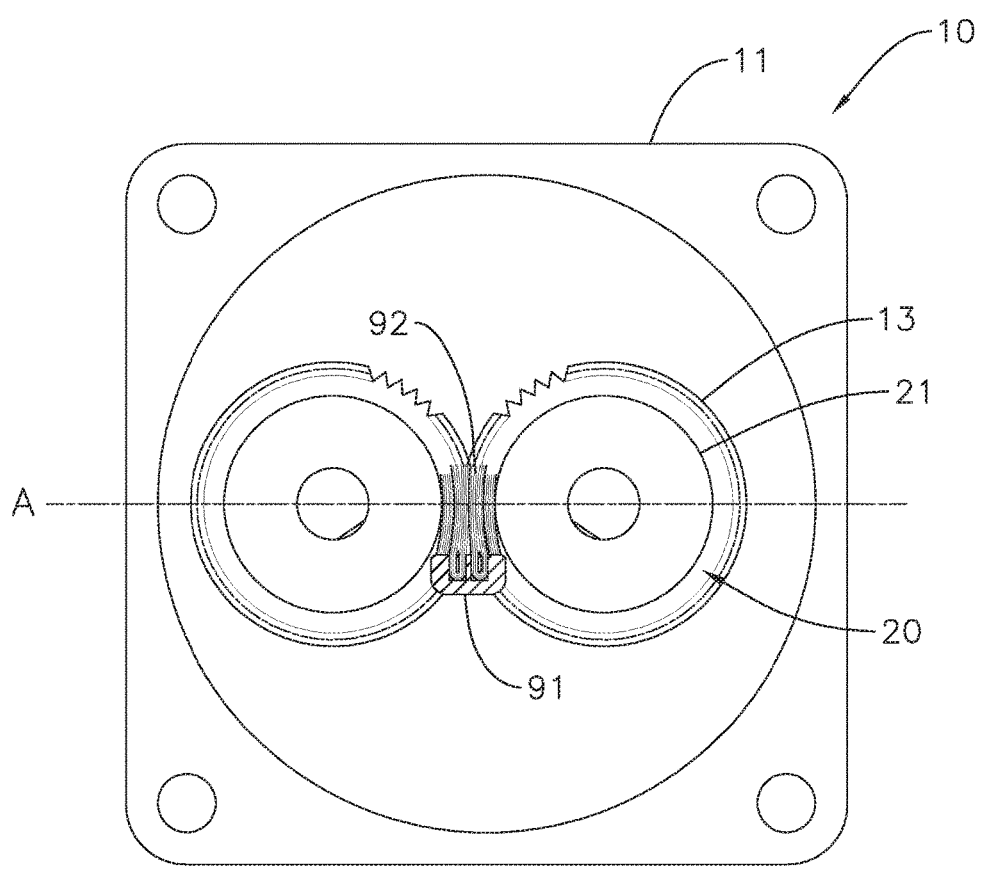
FIG. 3 is a cross sectional front view of the detecting machine in FIG. 1, with a toothbrush being detected.
Figure 4:
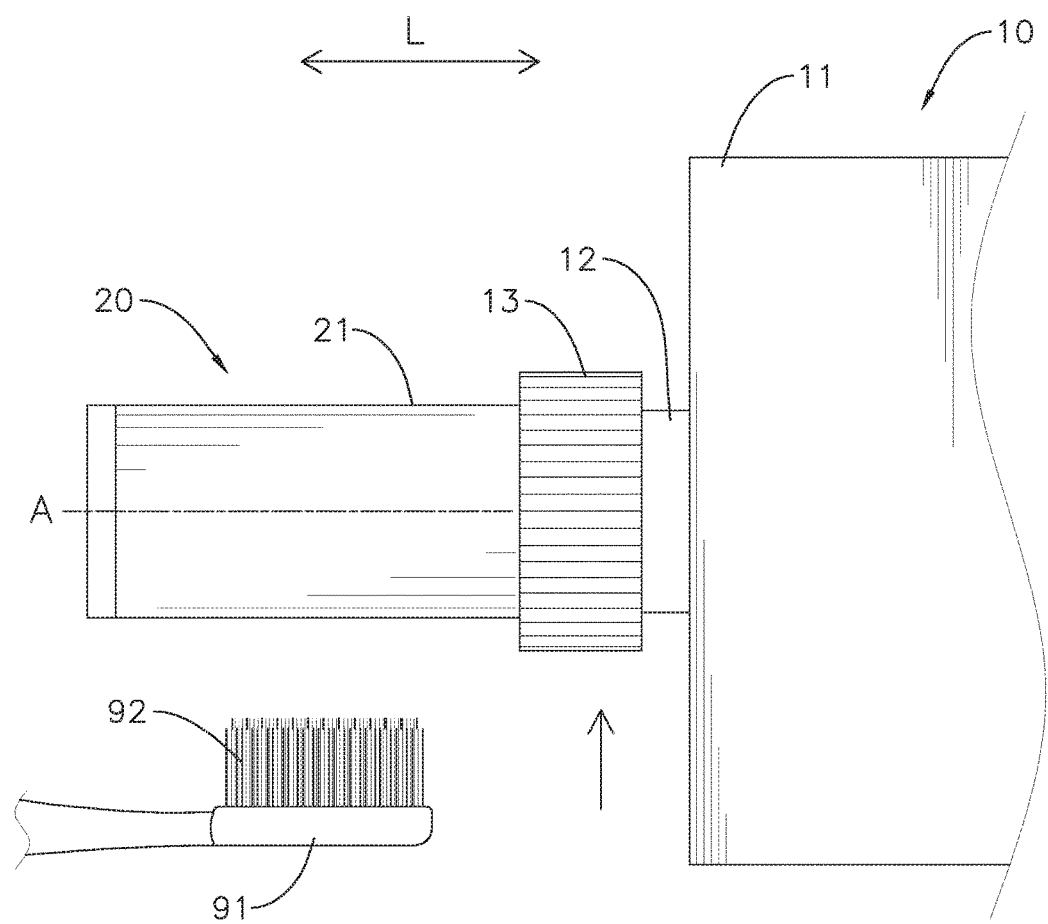
FIG. 4 is a side view of the detecting machine in FIG. 1, with a toothbrush being detected.

With reference to FIG. 3 and FIG. 4, an imaginary plane A is defined by the two rotating units 20. The imaginary plane A is a plane formed by the two axes of the two rotating units 20. In a rotating condition, the two rotating units 20 are driven by the motor 11 and rotate in opposite directions, therefore a portion of a surface 21 of each one of the two rotating units 20 may gradually pass through the imaginary plane A.

With reference to FIG. 3 and FIG. 4, in the rotating condition, the manufacturer can move a toothbrush 91 to a middle position between the two rotating units 20 and approach the two rotating units 20. When approaching the counter-rotating rotating units 20, the surfaces 21 of the two rotating units 20 compress two opposite sides of bristles 92 of the toothbrush 91 gradually, and therefore the two rotating units 20 pull the bristles 92 away from the head of the toothbrush 91 constantly.

With reference to FIG. 1 to FIG. 4, the detecting method for bristles of a toothbrush comprises several steps as follows. First, two rotating units 20 are prepared. The two rotating units 20 are preferably identical to the aforementioned two rotating units 20, but it is not limited thereto. The detailed structure of the two rotating units 20 is not repeated in the description.

Then, dispose the toothbrush 91 between the two rotating units 20. Because of the counter-rotating path of the two rotating units 20, when the two surfaces 21 compress the bristles 92 from opposite sides of the bristles 92, the constant rotating surfaces 21 will then compress and pull the bristles 92 away from the head of the toothbrush 91.

Under this detecting method, the pulling process may simulate the actual circumstance of tooth brushing, wherein the bristles 92 may be pulled back and forth when the users are brushing their teeth. Therefore, after the detecting process, the qualified toothbrush 91 may be determined by the amount of the bristles 92 which have been pulled away from the head of the toothbrush 91. Specifically, if the amount of the bristles 92 which have been pulled away from head of the toothbrush 91 is more than a preset value, said toothbrush may be determined as an unqualified product. By this detecting method, the yield rate of the toothbrush may be more precisely determined, wherein the manufacturer can reduce the chance of mistaking unqualified toothbrushes as qualified ones. Meanwhile, because the present detecting method is an auto-detecting method, it may be combined in an automated assembly line, thereby enhancing the efficiency of the production.

With reference to FIG. 3 and FIG. 4, in a preferred embodiment, when viewed from the front (as shown in FIG. 1), the rotating direction of the rotating unit 20 on a left side is counterclockwise, and the rotating direction of the rotating unit 20 on a right side is clockwise. Therefore, a side of the surface 21 of the right rotating unit 20 which is adjacent to a side of the surface 21 of the left rotating unit 20 moves upwardly, and so does the side of the surface 21 of the left rotating unit 20 which is adjacent to said side of the right rotating unit 20. Consequently, the toothbrush 91 to be detected should be placed under the two rotating units 20 at the start of the detecting process and gradually moves upwardly to approach the position between the two rotating units 20. By doing so, when the bristles 92 of the toothbrush 91 are placed horizontally between the two surfaces 21 of the two rotating units 20, the bristles 92 may be compressed by the two rotating units 20 and be pulled upwardly and away from the head of the toothbrush 91. The rotating directions of the two rotating units 20 are not limited thereto, as long as the two rotating units rotate in directions opposite to each other, so the toothbrush may alternatively approach the rotating units 20 from the top of the two rotating units 20.

Even though numerous characteristics and advantages of the present invention have been set forth in the foregoing description, together with details of the structure and features of the invention, the disclosure is illustrative only. Changes may be made in the details, especially in matters of shape, size, and arrangement of parts within the principles of the invention to the full extent indicated by the broad general meaning of the terms in which the appended claims are expressed.

What is claimed is:

1. A detecting machine for a yield rate of bristles of a toothbrush, the detecting machine comprising:
   a power device; and
   two rotating units rotatably mounted on a side surface of the power device, disposed parallel to each other, and being capable of being driven by the power device to rotate respectively, wherein an outer surface of each one of the two rotating units is a smooth surface;

wherein when each one of the two rotating units is in a rotating condition, the two rotating units rotate in opposite rotating directions, a tuft of the bristles of the toothbrush is moved to a position between the two rotating units, and the outer surfaces of the two rotating units jointly compress the tuft of bristles.

2. A detecting method for bristles of a toothbrush comprising steps as follows:
- moving a tuft of the bristles of the toothbrush to a position between two rotating units;
- rotating the two rotating units in different rotating directions respectively, wherein an outer surface of each one of the two rotating units is a smooth surface;
- compressing two opposite sides of the tuft of bristles respectively and pulling the bristles toward a direction away from a head of the toothbrush by the outer surfaces of the two rotating units.

\* \* \* \* \*